US012016526B2

(12) United States Patent
Matsuo (10) Patent No.: US 12,016,526 B2
(45) Date of Patent: Jun. 25, 2024

(54) MUCOUS MEMBRANE LIFTING INSTRUMENT AND MUCOUS MEMBRANE LIFTING METHOD

(71) Applicant: OLYMPUS CORPORATION, Hachioji (JP)

(72) Inventor: Nobuko Matsuo, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 815 days.

(21) Appl. No.: 16/934,079

(22) Filed: Jul. 21, 2020

(65) Prior Publication Data

US 2020/0345379 A1 Nov. 5, 2020

Related U.S. Application Data

(63) Continuation of application No. PCT/JP2018/020740, filed on May 30, 2018.

(51) Int. Cl.
 *A61B 1/00* (2006.01)
 *A61B 1/018* (2006.01)
 (Continued)

(52) U.S. Cl.
 CPC .......... *A61B 1/00089* (2013.01); *A61B 1/018* (2013.01); *A61B 17/12013* (2013.01);
 (Continued)

(58) Field of Classification Search
 CPC .............. A61B 1/0008; A61B 1/00087; A61B 1/00089; A61B 1/00101; A61B 17/12;
 (Continued)

(56) References Cited

U.S. PATENT DOCUMENTS 5,269,789 A * 12/1993 Chin ................ A61B 17/12013
 606/140
5,320,630 A * 6/1994 Ahmed ............ A61B 17/12013
 600/101
(Continued)

FOREIGN PATENT DOCUMENTS

JP H09-508299 A 8/1997
JP H10-272091 A 10/1998
(Continued)

OTHER PUBLICATIONS

Apr. 27, 2021 Office Action issued in Japanese Patent Application No. 2020-522452.
(Continued)

*Primary Examiner* — Ryan N Henderson
(74) *Attorney, Agent, or Firm* — Oliff PLC (57) ABSTRACT

A mucous membrane lifting instrument includes: a tubular hood having a proximal end attachable to a distal end of an endoscope; a first band having an elasticity, and arranged on an outer peripheral surface of the hood in a stretched state; a second band having an elasticity, and arranged on the outer peripheral surface of the hood in a stretched state at a position proximal of the first band; and a linear member that is connected to the first band, and passes between the outer peripheral surface of the hood and the second band.

16 Claims, 5 Drawing Sheets

(51) Int. Cl.
*A61B 17/12* (2006.01)
*A61B 17/221* (2006.01)
*A61B 17/00* (2006.01)
*A61B 17/30* (2006.01)

(52) U.S. Cl.
CPC .. *A61B 17/221* (2013.01); *A61B 2017/00269* (2013.01); *A61B 2017/00296* (2013.01); *A61B 2017/00818* (2013.01); *A61B 2017/12018* (2013.01); *A61B 2017/2212* (2013.01); *A61B 2017/306* (2013.01)

(58) Field of Classification Search
CPC ........ A61B 17/12009; A61B 17/12013; A61B 2017/12004; A61B 2017/12018
See application file for complete search history.

(56) References Cited

U.S. PATENT DOCUMENTS

| | | | | |
|---|---|---|---|---|
| 5,356,416 A * | 10/1994 | Chu | A61B 17/12013 | 606/140 |
| 5,398,844 A * | 3/1995 | Zaslavsky | A61B 17/12013 | 606/140 |
| 5,462,559 A * | 10/1995 | Ahmed | A61B 17/12013 | 606/139 |
| 5,569,268 A * | 10/1996 | Hosoda | A61B 17/12013 | 606/139 |
| 5,624,453 A * | 4/1997 | Ahmed | A61B 17/12013 | 606/139 |
| 5,788,715 A * | 8/1998 | Watson, Jr. | A61B 17/12013 | 606/140 |
| 5,853,416 A * | 12/1998 | Tolkoff | A61B 17/12013 | 606/140 |
| 5,857,585 A * | 1/1999 | Tolkoff | A61B 17/12013 | 221/36 |
| 5,913,865 A * | 6/1999 | Fortier | A61B 17/12013 | 606/140 |
| 5,968,056 A * | 10/1999 | Chu | A61B 18/14 | 606/139 |
| 5,976,158 A * | 11/1999 | Adams | A61B 17/12013 | 606/140 |
| 5,980,537 A * | 11/1999 | Ouchi | A61B 17/12013 | 606/140 |
| 6,007,551 A * | 12/1999 | Peifer | A61B 17/12013 | 606/139 |
| 6,042,591 A * | 3/2000 | Mears | A61B 17/12013 | 606/140 |
| 6,059,797 A * | 5/2000 | Mears | A61B 17/12009 | 606/139 |
| 6,136,009 A * | 10/2000 | Mears | A61B 17/12009 | 606/140 |
| 6,235,040 B1 * | 5/2001 | Chu | A61B 17/12013 | 606/139 |
| 6,280,452 B1 * | 8/2001 | Mears | A61B 17/12013 | 606/139 |
| 6,436,108 B1 * | 8/2002 | Mears | A61B 17/12013 | 606/139 |
| 6,464,708 B1 * | 10/2002 | Higuma | A61B 17/12013 | 606/139 |
| 6,676,672 B2 * | 1/2004 | Chu | A61B 17/12013 | 606/139 |
| 6,685,713 B1 * | 2/2004 | Ahmed | A61B 17/12013 | 606/139 |
| 6,730,101 B1 * | 5/2004 | Peifer | A61B 17/12013 | 606/139 |
| 6,974,466 B2 * | 12/2005 | Ahmed | A61B 17/12013 | 606/139 |
| 7,063,709 B2 * | 6/2006 | Fortier | A61B 17/12013 | 606/139 |
| 7,150,752 B2 * | 12/2006 | Suzuki | A61B 17/12013 | 600/149 |
| 7,488,333 B2 * | 2/2009 | Ghareeb | A61B 17/12013 | 606/140 |
| 7,727,249 B2 * | 6/2010 | Rahmani | A61B 17/12013 | 606/140 |
| 8,062,308 B2 * | 11/2011 | Noda | A61B 17/12013 | 128/831 |
| 8,097,003 B2 * | 1/2012 | Hoffman | A61B 1/00087 | 606/139 |
| 8,262,677 B2 * | 9/2012 | Goto | A61B 17/12013 | 606/140 |
| 8,480,687 B2 * | 7/2013 | Ducharme | A61B 17/0057 | 606/140 |
| 8,496,578 B2 * | 7/2013 | Surti | A61B 17/12013 | 606/139 |
| 8,506,477 B2 * | 8/2013 | Waller | A61B 17/12013 | 600/129 |
| 8,728,096 B2 * | 5/2014 | Doughty | A61B 17/12013 | 606/140 |
| 8,764,768 B2 * | 7/2014 | Karpiel | A61B 17/10 | 227/175.1 |
| 8,821,515 B2 * | 9/2014 | Richardson | A61B 17/12013 | 606/151 |
| 8,845,516 B2 * | 9/2014 | Chami | A61B 17/12013 | 600/106 |
| 9,023,064 B2 * | 5/2015 | Vermeersch | A61B 17/12013 | 606/140 |
| 9,155,554 B2 * | 10/2015 | Smith | A61B 1/0008 | |
| 9,370,370 B2 * | 6/2016 | Abi-Kheirs | A61B 17/1227 | |
| 9,402,631 B2 * | 8/2016 | Knotts | A61B 17/12013 | |
| 9,474,531 B2 * | 10/2016 | Fortier | A61B 17/12013 | |
| 9,498,224 B2 * | 11/2016 | Mullins | A61B 1/00087 | |
| 10,105,143 B2 * | 10/2018 | Smith | A61B 17/12013 | |
| 2002/0072757 A1 * | 6/2002 | Ahmed | A61B 17/12013 | 606/139 |
| 2003/0229359 A1 * | 12/2003 | Fortier | A61B 17/12013 | 606/139 |
| 2004/0006256 A1 * | 1/2004 | Suzuki | A61B 1/00133 | 600/140 |
| 2005/0143757 A1 * | 6/2005 | Ghareeb | A61B 17/12013 | 606/139 |
| 2005/0177178 A1 * | 8/2005 | Suzuki | A61B 17/12013 | 606/144 |
| 2006/0129167 A1 * | 6/2006 | Fortier | A61B 17/12013 | 606/140 |
| 2006/0259041 A1 * | 11/2006 | Hoffman | A61B 1/00087 | 606/139 |
| 2007/0118162 A1 * | 5/2007 | Abi-Kheirs | A61B 17/1227 | 606/157 |
| 2007/0260112 A1 * | 11/2007 | Rahmani | A61B 17/12013 | 600/104 |
| 2007/0265493 A1 * | 11/2007 | Zirps | A61B 17/12013 | 606/140 |
| 2008/0091218 A1 * | 4/2008 | Richardson | A61B 17/12013 | 606/140 |
| 2008/0097478 A1 * | 4/2008 | Doughty | A61B 17/12013 | 606/140 |
| 2008/0108874 A1 * | 5/2008 | Waller | A61B 17/12013 | 606/140 |
| 2008/0255412 A1 * | 10/2008 | Surti | A61B 17/12013 | 606/140 |
| 2009/0105728 A1 * | 4/2009 | Noda | A61B 17/12013 | 606/151 |
| 2009/0125037 A1 * | 5/2009 | Goto | A61B 17/12013 | 606/140 |
| 2009/0131748 A1 * | 5/2009 | Chami | A61B 17/12013 | 600/106 |
| 2010/0057101 A1 * | 3/2010 | Karpiel | A61B 17/0643 | 606/140 |
| 2011/0106116 A1 * | 5/2011 | Ducharme | A61B 17/0057 | 606/151 |
| 2013/0274766 A1 * | 10/2013 | Isaacson | A61B 17/00 | 606/1 |
| 2014/0058410 A1 * | 2/2014 | Vermeersch | A61B 17/12013 | 606/140 |

(56) References Cited

U.S. PATENT DOCUMENTS

| | | | | |
|---|---|---|---|---|
| 2014/0142596 A1* | 5/2014 | Knotts | ............. | A61B 17/00234 |
| | | | | 606/140 |
| 2014/0249550 A1* | 9/2014 | Mullins | ............ | A61B 17/12013 |
| | | | | 606/140 |
| 2016/0220258 A1* | 8/2016 | Xu | ................... | A61B 17/12013 |

FOREIGN PATENT DOCUMENTS

| | | | |
|---|---|---|---|
| JP | 2005-103107 | A | 4/2005 |
| JP | 2006-280849 | A | 10/2006 |
| JP | 2008-155006 | A | 7/2008 |
| WO | 95/020464 | A1 | 8/1995 |

OTHER PUBLICATIONS

Aug. 14, 2018 International Search Report issued in PCT Application No. PCT/JP2018/020740.

* cited by examiner

MUCOUS MEMBRANE LIFTING INSTRUMENT AND MUCOUS MEMBRANE LIFTING METHOD

CROSS REFERENCE TO RELATED APPLICATIONS

This application is a continuation application based on a PCT Patent Application No. PCT/JP2018/020740, filed on May 30, 2018, the entire content of which is hereby incorporated by reference.

BACKGROUND

The treatment of endoscopically removing lesions of the gastrointestinal tract is widely spread as a radical treatment capable of collectively excising lesions while being minimally invasive.

In endoscopic submucosal dissection (ESD), the mucous membrane layer around the region containing the lesion is incised and then the submucous membrane layer is detached to excise the lesion. Further, as one of the procedures for resecting a region including a lesion without opening the lumen of the digestive tract using an endoscope and a laparoscope, Non-exposure Endoscopic Wall-inversion Surgery (NEWS) is known. Also in the NEWS procedure, the mucous membrane layer is incised under an endoscope, and the submucous membrane layer is subjected to detachment to excise the lesion.

In the submucous membrane layer peeling work, there is a need that the submucous membrane layer, which constitutes the innermost layer of the digestive tract, is appropriately pulled up to ensure that the submucous membrane layer is captured in the field of view of the endoscope, and also proceed while applying appropriate traction to the peeled site.

However, the inside of the digestive tract is an extremely limited space, and it is difficult to apply appropriate traction to the ablation site depending on the position of the lesion and the posture of the patient. For this reason, the peeling operation of the submucous membrane layer is difficult and time-consuming.

In a mucous membrane traction tool, a first sandwiching member can be attached to a mucous membrane layer to be incised and peeled off, and a second sandwiching member can be attached to a mucous membrane layer different from the mucous membrane layer to be incised and stripped off. The first sandwiching member and one end of an elastic portion are connected by a first connecting body, and the second sandwiching member and another end of the elastic portion are connected by a second connecting body, so that the elastic portion stretches to pull the mucous membrane layer to be incised and peeled off. The mucous membrane traction tool is used to pull the submucous membrane layer while pulling the mucous membrane layer in the region containing the lesion.

In the mucous membrane traction tool, the amount of traction force is defined by the restoring force of the elastic portion, and thus it is difficult to adjust the traction. In addition, since the first clamping member is attached to the mucous membrane to be incised and peeled off and the second clamping member is attached to another mucous membrane, it is difficult to make the distance between the mucous membrane to be incised and peeled off and the other mucous membrane be shorter than the length of the mucous membrane retractor.

From the above, it is difficult for the mucous membrane traction tool to change the amount of traction and the size of traction during the separation.

SUMMARY

The present disclosure relates to a mucous membrane lifting instrument and a mucous membrane lifting method.

The present disclosure provides a mucous membrane lifting instrument and a mucous membrane lifting method that can easily change the amount of traction of the mucous membrane or the size of traction even during mucous membrane peeling.

According to an aspect, a mucous membrane lifting instrument is provided. The mucous membrane lifting instrument includes: a tubular hood having a proximal end attachable to a distal end of an endoscope; a first band having an elasticity, and arranged on an outer peripheral surface of the hood in a stretched state; a second band having an elasticity, and arranged on the outer peripheral surface of the hood in a stretched state at a position proximal of the first band; and a linear member that is connected to the first band, and passes between the outer peripheral surface of the hood and the second band.

According to another aspect, a mucous membrane lifting method by operating a mucous membrane lifting instrument is provided. The method includes: fixing the first band to the mucous membrane by removing the first band from the hood in a state in which a part of the mucous membrane is pulled into the hood; and then fixing the second band to a tube wall of a gastrointestinal tract by removing the second band from the hood in a state in which a part of the tube wall facing the mucous membrane is pulled into the hood, after the first band fixing step. When the second band is fixed to the tube wall, the linear member passes between the tube wall and the second band, and is supported by being sandwiched between the tube wall and the second band. Thereafter, an end of the linear member can be pulled to lift the mucous membrane.

According to the present disclosure, the amount of traction of the mucous membrane and the size of the traction can be easily changed even during the mucous membrane peeling.

DETAILED DESCRIPTION OF PREFERRED EMBODIMENTS

An embodiment of the present disclosure will be described with reference to FIGS. 1 to 10.

Figure 1:
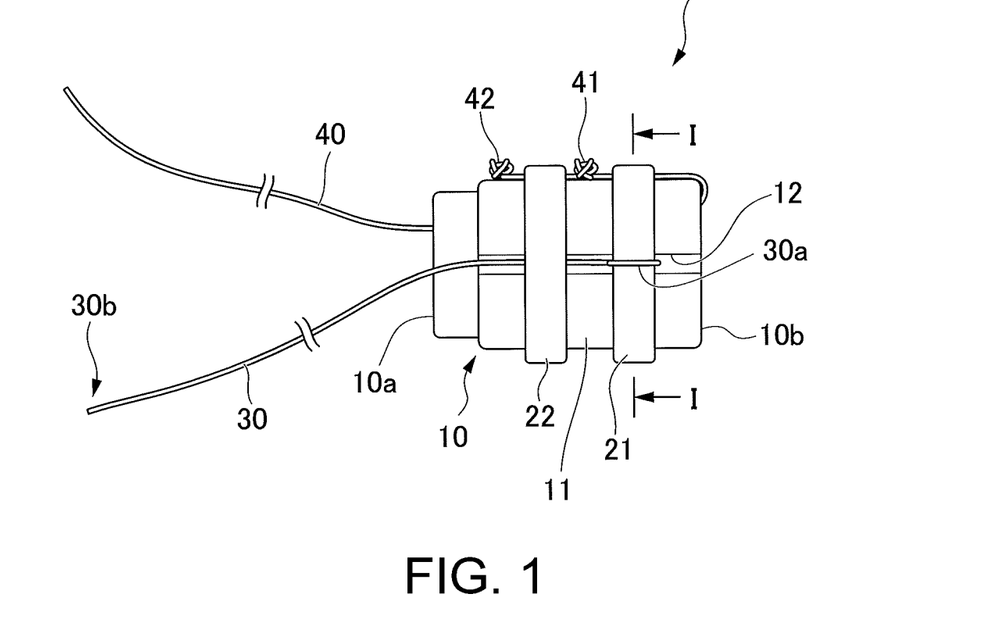
FIG. 1 is a view showing a mucous membrane lifting instrument according to an exemplary embodiment.
Figure 2:
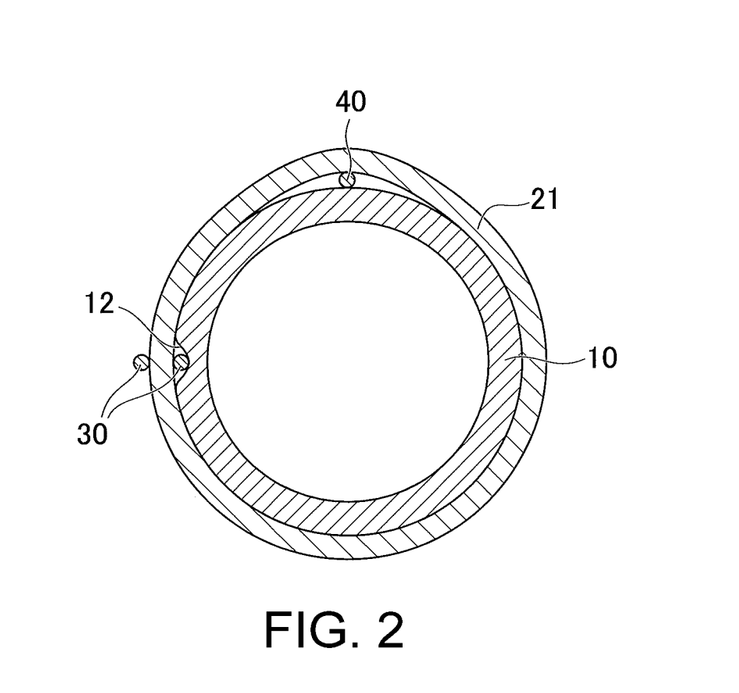
FIG. 2 is a cross-sectional view taken along the line I-I of FIG. 1.

FIG. 1 is a view showing a mucous membrane lifting instrument 1 of this embodiment. FIG. 2 is a sectional view taken along the line I-I of FIG. 1. As shown in FIG. 1, the mucous membrane lifting instrument 1 includes a hood 10, a first band 21 and a second band 22 attached to the hood 10, a linear member 30 arranged between the hood 10, the first band 21 and the second band 22, and a band operating member 40.

The hood 10 is a tubular member made of resin, metal, or the like. The hood 10 can be attached to the distal end of the endoscope by fitting the first end portion (proximal end) 10a of the tubular shape of the hood 10 in the axial direction into the endoscope insertion portion. A groove 12 extending substantially parallel to the axis of the hood 10 is formed on the outer peripheral surface 11 of the hood 10.

The first band 21 and the second band 22 are annular members made of a material having elasticity. As the material having elasticity, rubber or elastomer can be used. The first band 21 and the second band 22 have an outer diameter smaller than the outer diameter of the hood 10 in a state where no external force is applied (hereinafter, natural state). The first band 21 and the second band 22 are mounted on the outer peripheral surface 11 by passing the hood 10 in a state of being extended to an outer diameter larger than the outer diameter of the hood 10 and then partially releasing the progress. The first band 21 and the second band 22 are not completely released when they are attached to the hood 10. The second band 22 is attached to a position closer to the first end 10 a than the first band 21, and covers a part of the groove 12.

The materials of the first band 21 and the second band 22 may be different. The first band 21 and the second band 22 may have different dimensions in a natural state.

The linear member 30 is, for example, a thread, a string, a wire, or the like. The first end 30a of the linear member 30 is tied to and fixed to the first band 21. As shown in FIG. 2, the linear member 30 is arranged in the groove 12 and extends through between the second band 22 and the outer peripheral surface 11. In the present embodiment, the width and depth of the groove 12 are equal to or larger than the diameter of the linear member 30. Therefore, the linear member 30 housed in the groove 12 does not project on the outer peripheral surface 11 having a substantially cylindrical shape.

As shown in FIG. 1, the second end 30b of the linear member 30 is arranged so as to extend toward the proximal end side of the endoscope when the hood 10 is attached to the endoscope. The length of the linear member 30 may be equal to or longer than that required for lifting the mucous membrane, which will be described later. The length of the linear member 30 is, for example, 10 cm or more.

The band operating member 40 is, for example, an elongated member having a thickness that can be inserted into a channel formed in the endoscope. In this case, the band operating member 40 has two knots, the first knot 41 and the second knot 42. A part 40 of the band operating member is arranged between the outer peripheral surface 11 and the first band 21 and the second band 22. The first and second knots 41 and 42 are not limited to knots, but instead may be any element or portion of the band operating member 40 having a larger diameter than a distal end of the band operating member 40.

The first knot 41 is located between the first band 21 and the second band 22. The second knot 42 is located between the second band 22 and the first end portion 10a. The rest of the band operating member 40 extends from the first band 21 toward the second end (distal end) 10b, folds back at the second end 10b, enters the hood 10, and passes through the hood 10. The length of the remaining portion is longer than the length of the channel of the endoscope to be mounted.

The mucous membrane lifting method of this embodiment will be described. The mucous membrane lifting method is performed using the mucous membrane lifting instrument 1 of the present embodiment, First, an operator or an assistant attaches the mucous membrane lifting instrument 1 to the endoscope 100 (see FIG. 3). The first end 10a of the hood 10 is fitted to the distal end of the endoscope 100, and the remaining portion of the band operating member 40 is inserted from the distal end opening of the channel of the endoscope 100 and pulled out from the proximal opening of the channel.

The operator inserts the endoscope 100 to which the mucous membrane lifting instrument 1 is attached into the digestive tract of the patient, and advances the distal end of the endoscope 100 to near the lesion to be treated. The operator observes the lesion with the endoscope 100, examines the size of the margin around the lesion, and determines the position and size of the mucous membrane to be resected. Then, the incision tool 110 (see FIG. 7) such as a high frequency knife is inserted into the channel of the endoscope 100 to project the incision tool 110 from the distal end opening. While observing the mucous membrane and the lesion with the endoscope 100, the mucous membrane is marked using the incision tool 110, and then the surrounding area is incised.

Figure 3:
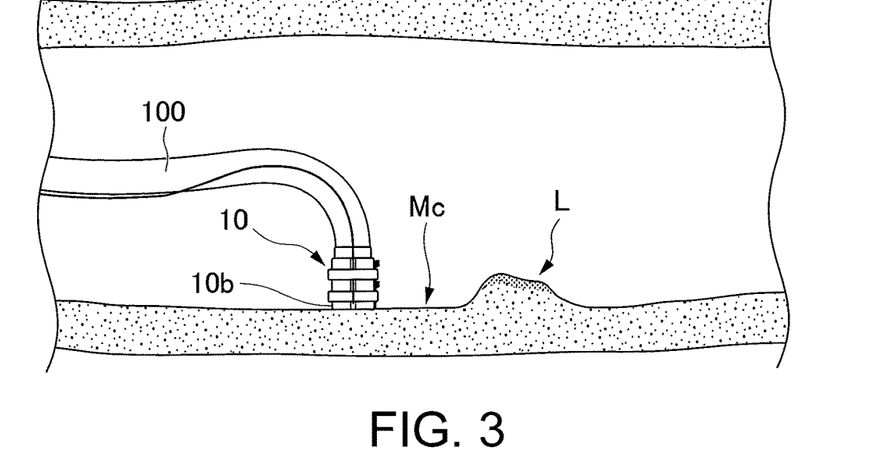
FIG. 3 is a diagram showing a process of using the mucous membrane lifting instrument.

Subsequently, the operator fixes the first band 21 to the mucous membrane to be excised (first band fixing step). The operator moves the endoscope to bring the entire second end 10b of the hood 10 into contact with the mucous membrane Mc within the excision range, as shown in FIG. 3. The position of contact is preferably the mucous membrane Mc within the resection range that is closest to the distal end of the endoscope when the lesion L is captured within the observation field of the observation optical system of the endoscope.

The operator operates the endoscope 100 to suck the mucous membrane in a state where the second end 10b is in contact with the mucous membrane. By suction, a part of the mucous membrane is drawn into the hood 10 and rises in the digestive tract. When a surgeon pulls the band operating member 40 extending from the proximal side opening of the channel with a part of the mucous membrane entering the hood 10, the first knot 41 approaches the second end 10b of the hood 10. The first knot 41 comes into contact with the first band 21, moves the first band 21 toward the second end portion 10b, and finally disengages the first band 21 from the hood 10.

Figure 4:
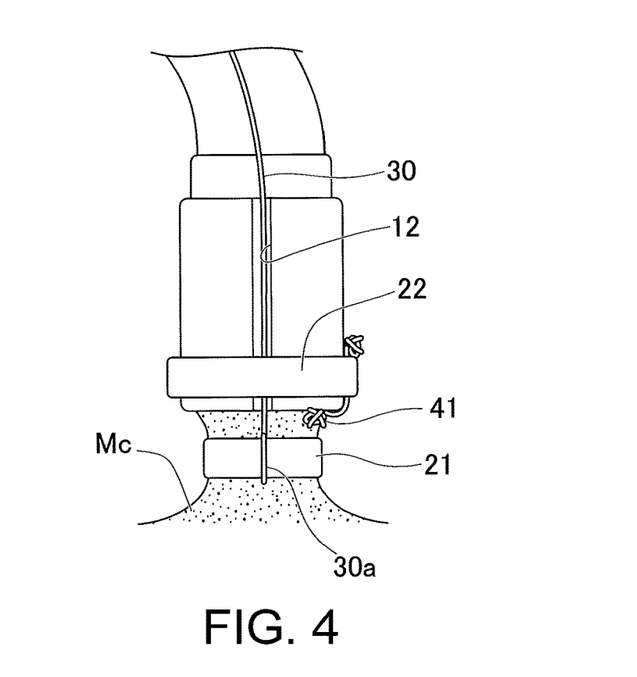
FIG. 4 is a diagram showing a first band fixing step in a mucous membrane lifting method using the same mucous membrane lifting instrument.

The first band 21 removed from the hood 10 is restored to a shape close to a natural state, and the outer diameter and the inner diameter are reduced. As a result, as shown in FIG. 4, the first band 21 clamps the root of the mucous membrane Mc sucked into the hood 10 and is fixed to the mucous membrane Mc. When the operator stops sucking the endoscope 100, the first end 30a of the linear member 30 is fixed to the mucous membrane by the first band 21.

Figure 5:
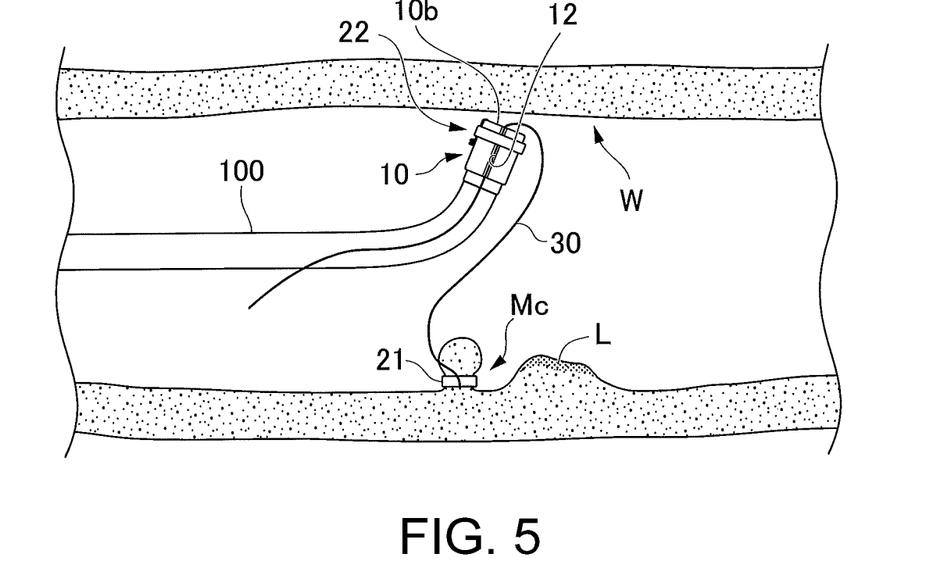
FIG. 5 is a diagram showing a second band fixing step in the method for lifting a mucous membrane.

Next, the operator moves the distal end of the endoscope 100 toward the tube wall W of the digestive tract that faces the mucous membrane Mc. By the movement of the distal end portion of the endoscope 100, the hood 10 and the first band 21 are separated from each other as shown in FIG. 5, and the linear member 30 is pulled out from the second band 22 toward the second end portion 10b side. Since the linear member 30 is arranged in the groove 12, the linear member 30 can be smoothly pulled out without causing much friction with the second band 22.

Subsequently, the operator fixes the second band 22 to the tube wall W facing the mucous membrane Mc (second band fixing step). The operator advances the endoscope 100 to bring the entire second end 10b of the hood 10 into contact with the tube wall W.

Then, the tube wall W is sucked by the endoscope 100, and a part of the tube wall W is drawn into the hood 10. When the operator pulls the band operating member 40 with a part of the tube wall W entering the inside of the hood 10, the second knot 42 approaches the second end 10b of the hood 10. The second knot 42 comes into contact with the second band 22 to move the second band 22 toward the second end portion 10b, and finally disengage the second band 22 from the hood 10. As a result, the second band 22 tightens the root of the tube wall W sucked into the hood 10 and is fixed to the tube wall W. The linear member 30 is sandwiched between the tube wall W and the second band 22, and is supported by the tube wall W by a frictional force.

Figure 6:
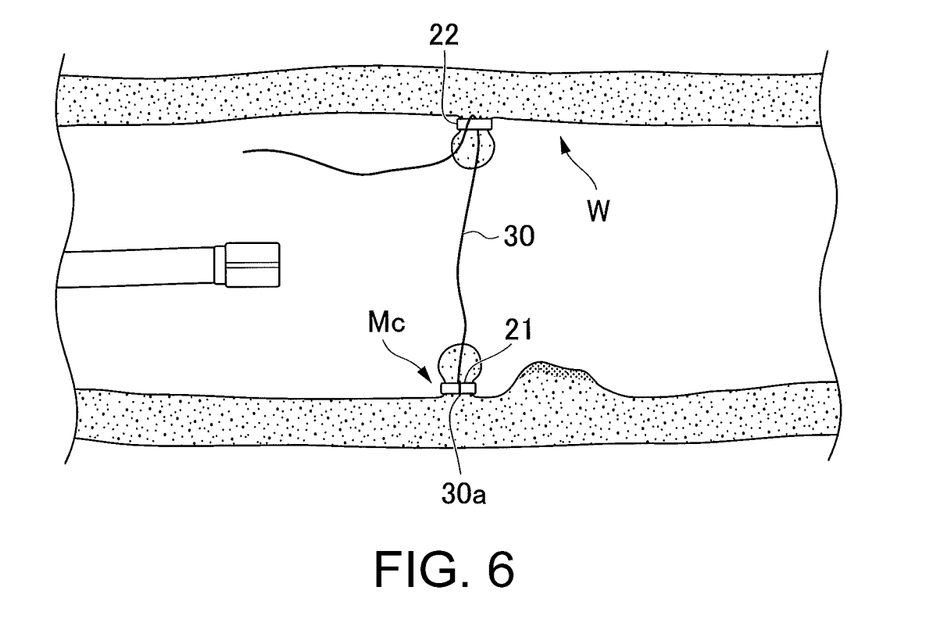
FIG. 6 is a diagram showing a state after the second band fixing step.

When the second band fixing step is completed, the linear member 30 extends from the mucous membrane Mc toward the tube wall W with the first end 30a fixed to the mucous membrane Mc, as shown in FIG. 6, the second band 22 and the second band 22 are further extended.

Figure 7:
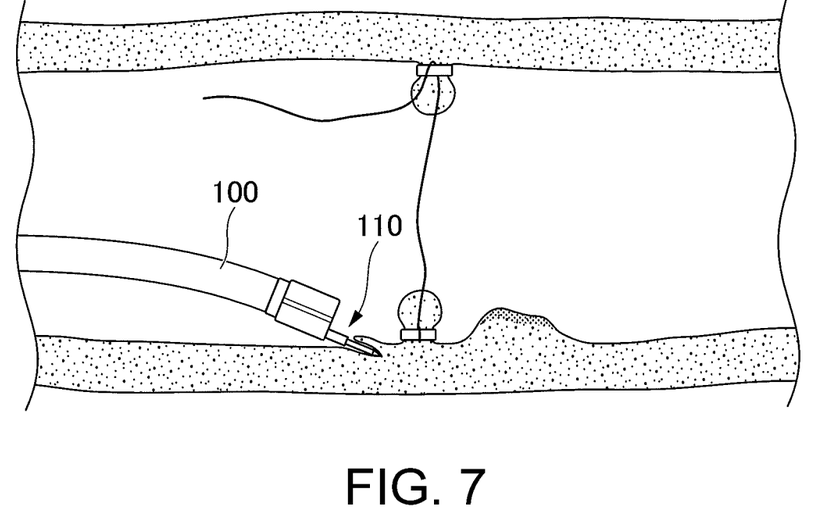
FIG. 7 is a diagram showing a state in which the submucous membrane layer is peeled off.

Subsequently, the operator removes the band operating member 40 from the channel. Further, a cutting tool such as a high-frequency knife is inserted into the channel to project the cutting tool from the distal end opening. As shown in FIG. 7, the operator uses the incision tool 110 to sequentially peel off the submucous membrane layer under the mucous membrane Mc from the incised portion. If necessary, swelling of the site to be excised using physiological saline or the like is also performed. The incision of the mucous membrane and the peeling of the submucous membrane layer can be performed in the same manner as the procedure in ESD or the like.

Figure 8:
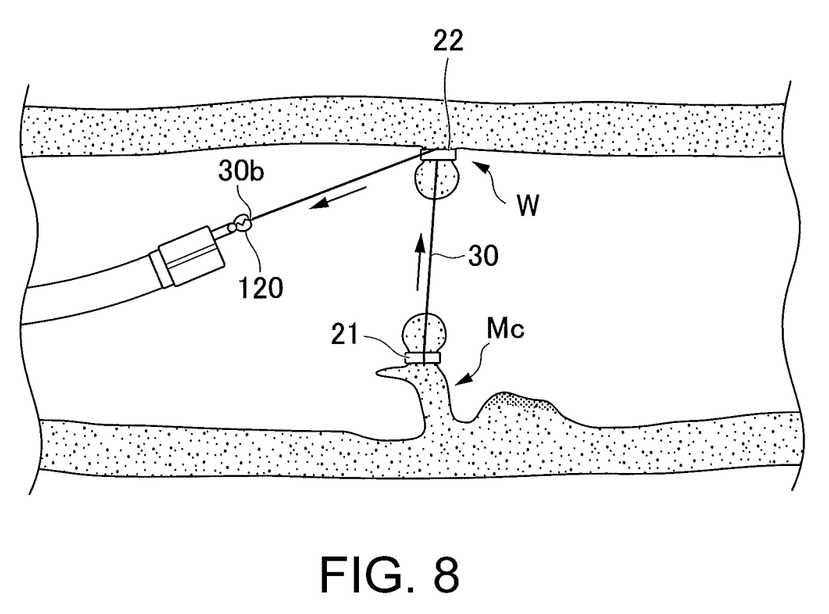
FIG. 8 is a diagram showing a state in which the mucous membrane is lifted.

When the peeling of the submucous membrane layer proceeds, the mucous membrane in the already peeled portion hinders the procedure, and thus the mucous membrane Mc is lifted. The operator removes the incision tool 110 from the channel and inserts the grasping forceps into the channel. The operator grasps the linear member 30 extending between the tube wall W and the second band 22 with the grasping forceps 120 (see FIG. 8) protruding from the distal end opening, and pulls it in the direction of separating from the second band 22. The linear member 30 is supported by being sandwiched between the second band 22 and the tube wall W, but is not completely fixed. Therefore, when pulled by a force exceeding the above-mentioned frictional force, the linear member 30 moves with respect to the second band 22 and the tube wall W. When the linear member 30 moves, the first band 21 connected to the linear member 30 approaches the tube wall W while being fixed to the mucous membrane Mc. As a result, as shown in FIG. 8, the mucous membrane Mc is lifted (mucous membrane lifting step). The linear member 30 is supported between the tube wall W and the second band 22 so as to support the load of the lifted mucous membrane Mc and hold the position of the mucous membrane Mc.

The pulling amount of the linear member 30 in the mucous membrane lifting step may be appropriately determined by the operator in consideration of the amount of peeling, the size of the mucous membrane Mc to be excised, the size of the traction desired to be lifted on the mucous membrane, and the like. If the linear member 30 is pulled too much, a portion of the linear member 30 located between the second band 22 and the first band 21 can be pulled in the direction in which the linear member 30 is separated from the second band 22, that is, in the direction opposite to the above-described pulling.

Figure 9:
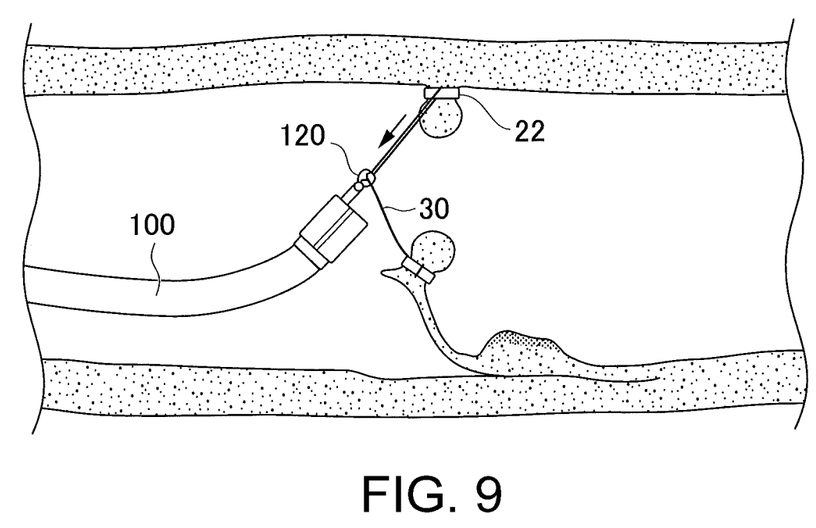
FIG. 9 is a diagram showing a step in using the same mucous membrane lifting instrument.

The operator appropriately operates the linear member 30 to further peel off the submucous membrane layer under the mucous membrane Mc while changing the lifting state of the mucous membrane and the size of the traction. After the peeling of the mucous membrane Mc in the predetermined range including the lesion L is completed, the operator, as shown in FIG. 9, grasps both of a portion of the linear member 30 extending between the tube wall W and the second band 22 and a portion located between the second band 22 and the first band 21, with the grasping forceps 120. When the operator pulls the linear member 30 in the direction away from the tube wall W as it is, the second band 22 and the linear member 30 are separated from the tube wall W.

After that, when the lesion L and the mucous membrane Mc that have been peeled off are collected outside the body, a series of procedures is completed. The lesion L and the mucous membrane Mc may be collected with the first band 21 fixed, or may be collected after removing the first band 22.

According to the mucous membrane lifting instrument 1 of the present embodiment, the hood 10 to which the first band 21 and the second band 22 are attached is provided, so that the mucous membrane lifting instrument 1 can be attached to the endoscope 100 to suck a desired mucous membrane or a tube wall. Thus, the linear member 30 can be easily arranged at the sucked portion. Therefore, depending on the position where the second band 22 is arranged, the direction in which the mucous membrane is pulled can be freely set. Further, regardless of the direction in which the mucous membrane is pulled, the mucous membrane can be lifted just by pulling the linear member 30 in the direction away from the second band 22, and the operability is good.

In addition, in the mucous membrane lifting method using the mucous membrane lifting instrument 1, the length of the linear member 30 located between the second band 22 attached to the tube wall W and the first band 21 attached to the mucous membrane can be freely changed. Therefore, unlike a known mucous membrane retractor, the size of the traction applied to the mucous membrane is less likely to be affected by the physical properties of the linear member 30. As a result, the size of the traction can be adjusted easily and freely.

Furthermore, since the linear member 30 is supported on the mucous membrane and the tube wall by the first band 21 and the second band 22, the method of the present disclosure is less invasive than the method of locking the linear member 30 with a tag, a clip or the like on the mucous membrane and the tube wall, and is easy to remove.

The linear member 30 is arranged in the groove 12 formed on the outer peripheral surface 11 of the hood 10 and does not project onto the outer peripheral surface 11. As a result, when the distal end of the endoscope 100 approaches the tube wall W after the first band 21 is fixed to the mucous membrane Mc, the linear member 30 and the second band 22 are unlikely to cause friction, and the linear member 30 can be smoothly pulled out.

Various changes may be made to the mucous membrane lifting instrument and the mucous membrane lifting method according to the present embodiment. Although some modifications are illustrated below, these are not all and other modifications are possible. Two or more of these changes may be combined appropriately.

(1) In the first band fixing step and the second band fixing step, instead of sucking a part of the mucous membrane or the tube wall and pulling it into the hood, it may be held by the grasping forceps and pulled into the hood.

(2) When the endoscope has a plurality of channels, grasping forceps may be passed through a channel different from the channel through which the incision tool passes. In this case, it is not necessary to replace the incision tool and the grasping forceps in the mucous membrane lifting step, and the required time can be shortened and the mucous membrane can be easily lifted.

(3) A loop, a knot, or the like may be provided at the second end of the linear member 30 or a portion near the second end to facilitate grasping with the grasping forceps.

(4) In the mucous membrane lifting step, the operation of the linear member 30 may be performed by an instrument other than the grasping forceps. For example, when the distal end of the incision tool has a hook shape, a loop or knot may be provided on the linear member as described above, and the hook may be hung on the loop or knot to pull the linear member. The linear member may be pulled by suction, for example, by attaching a member capable of being sucked to the endoscope distal end portion by suction to the linear member. Also in these cases, it is not necessary to replace the incision tool with the grasping forceps.

(5) In addition, the second end of the linear member 30 may be pulled out to the outside of the patient's body. In this case, in the mucous membrane lifting step, the operator or an assistant can lift the mucous membrane by grasping and pulling the second end, so the mucous membrane can be lifted without using grasping forceps, and the operation is simple.

(6) The first end of the linear member may be fixed to the first band with an adhesive or the like.

(7) The groove 12 does not need to be substantially parallel to the axis of the hood 10. As long as the second band 22 is wrapped around the hood 10 and intersects with a part of the groove 12, the above-described friction reducing effect is achieved.

(8) The groove 12 may have a size such that the linear member 30 is not completely housed therein. Also in this case, a certain effect of reducing the friction with the second band 22 is obtained. Since the groove 12 is not essential in the mucous membrane lifting instrument 1, the groove 12 may not be provided when the surface of the linear member is smooth or the like.

(9) In place of the first knot and the second knot of the band operating member, a spherical or rod-shaped member may be attached to the band member and the first band and the second band may be moved by these members.

(10) A plurality of band operating members may be provided to configure the mucous membrane lifting instrument so that the first band and the second band can be more reliably removed from the hood. In this case, the band operating member having the knot and the band operating member to which the member is attached may be used in combination.

(11) The hood 10 may be formed in a tapered shape whose diameter gradually decreases toward the second end. With such a shape of the hood, the first band and the second band can be smoothly removed from the hood.

(12) The hood 10 may be removed to perform incision and peeling using the incision tool 110 and various operations using the grasping forceps 120.

Figure 10:
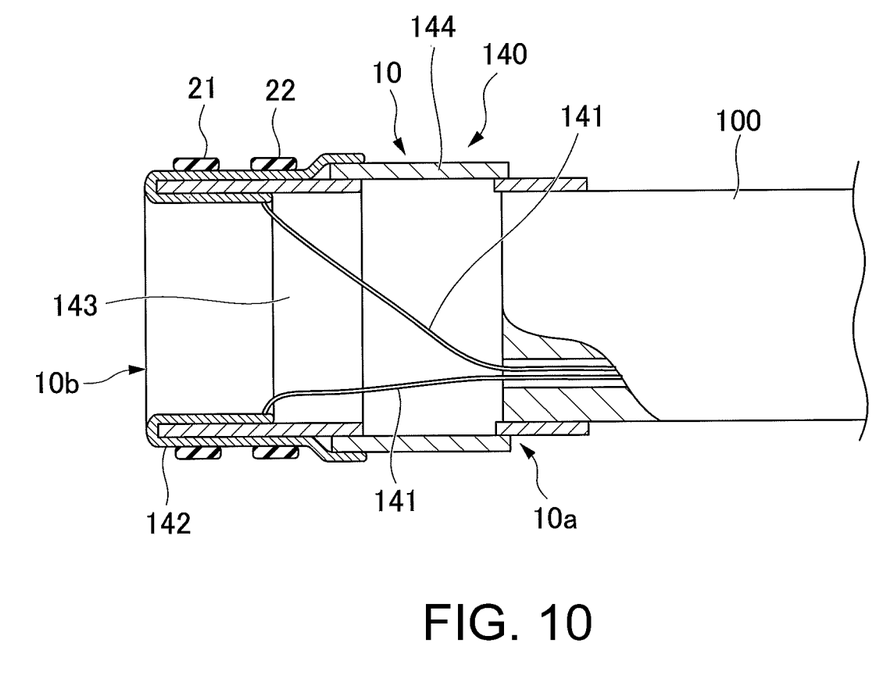
FIG. 10 is a diagram showing an exemplary band operating member.

FIG. 10 shows another configuration example of the band operating member. The band operating member 140 shown in FIG. 10 includes a thread 141 that is passed through a channel and a flexible sheet 142 that is connected to the thread 141. The hood 10 has an outer cylinder 144 and an inner cylinder 143. The inner cylinder 143 is slidably attached to the inner cavity of the outer cylinder 144. The distal end of the inner cylinder 143 projects from the second end 10b.

The seat 142 is formed in a tubular shape, and is arranged along the inner surface of the inner cylinder 143. A portion of the seat 142 protruding from the distal end of the inner cylinder 143 is folded back to cover the outer peripheral surface of the inner cylinder 143. The end of the folded sheet 142 is fixed to the outer peripheral surface 11 of the hood 10. The first band 21 and the second band 22 are arranged on the sheet 142 that covers the outer peripheral surface of the inner cylinder 143.

In the above configuration example, when the operator pulls the thread 141, the seat 142 connected to the thread 141 moves toward the first end portion 10a inside the inner cylinder 143. The seat 142 changes its direction at the second end 10b and is drawn into the hood 10. As a result, the inner cylinder 143 is pushed by the seat 142 and moves into the outer cylinder 144, and the amount of protrusion of the inner cylinder 143 from the outer cylinder 144 gradually decreases. As a result, the first band 21 and the second band 22 are detached from the inner cylinder 143 that is a part of the hood 10.

Also in this configuration example, the operator can remove the first band and the second band from the hood at a desired timing by operating the band operating member.

While preferred embodiments have been described and illustrated above, it should be understood that these are exemplary and are not to be considered as limiting. Additions, omissions, substitutions, and other modifications can be made without departing from the spirit or scope of the present disclosure. Accordingly, the disclosure is not to be considered as being limited by the foregoing description, and is only limited by the scope of the appended claims.

What is claimed is:

1. A mucous membrane lifting instrument, comprising:
a tubular hood having a proximal end configured to be attached to a distal end of an endoscope;
a first band having an elasticity, and arranged on an outer peripheral surface of the hood;
a second band having an elasticity, and arranged on the outer peripheral surface of the hood, the second band disposed proximally along the outer peripheral surface of the hood relative to the first band; and
a linear member fixed to the first band such that the linear member is not detached from the first band by removing the first band from the hood, the linear member passing between the outer peripheral surface of the hood and the second band.

2. The mucous membrane lifting instrument according to claim 1, further comprising:
a band operating thread configured to be operated to remove the first band and the second band from the hood by moving the first band and the second band toward a distal end of the hood.

3. The mucous membrane lifting instrument according to claim 2, wherein the band operating thread is configured to pass between: (i) each of the first band and the second band, and (ii) the outer peripheral surface of the hood.

4. The mucous membrane lifting instrument according to claim 1, further comprising:
   an elongate member including a first portion and a second portion, the second band being disposed between the first portion and the second portion,
   wherein the first portion and the second portion each have a larger diameter than a remainder of a distal end of the elongate member.

5. The mucous membrane lifting instrument according to claim 4, wherein the elongate member is configured to be retracted in a proximal direction such that the first portion contacts the first band and moves the first band in a distal direction to disengage the first band from the hood.

6. The mucous membrane lifting instrument according to claim 5, wherein the elongate member is configured to be further retracted in the proximal direction such that the second portion contacts the second band and moves the second band in the distal direction to disengage the second band from the hood after the first band has been disengaged.

7. The mucous membrane lifting instrument according to claim 4, wherein each of the first portion and the second portion is a knot.

8. The mucous membrane lifting instrument according to claim 1, wherein:
   the hood has a groove on the outer peripheral surface,
   the second band covers a part of the groove, and
   at least a part of the linear member is located between the second band and a bottom of the groove.

9. The mucous membrane lifting instrument according to claim 1, wherein the mucous membrane lifting instrument is configured to:
   remove the first band from the hood so as to fix the first band to a portion of the mucous membrane to be excised, and
   remove the second band from the hood so as to fix the second band to a tube wall of a digestive tract that faces the portion of the mucous membrane to which the first band is fixed such that the linear member extends from a first end connected to the first band through the second band so as to be supported between the tube wall of the digestive tract and the second band to such an extent that the portion of the mucous membrane to which the first band is attached can be held in a lifted state.

10. The mucous membrane lifting instrument according to claim 9, wherein an outer diameter of the first band and an outer diameter of the second band are reduced when the first band and the second band are removed from the hood.

11. The mucous membrane lifting instrument according to claim 1, further comprising:
   a second linear member including:
      a first knot disposed between the first band and the second band; and
      a second knot disposed proximally relative to the second band along a longitudinal direction of the hood, the second knot disposed distally relative to the first knot along an extending direction of the second linear member.

12. The mucous membrane lifting instrument according to claim 1, further comprising:
   a second linear member including:
      a first knot disposed between the first band and the second band;
      a second knot disposed proximally relative to the second band; and
      a middle part disposed distally relative to the first band and configured to be folded at a distal end of the hood.

13. The mucous membrane lifting instrument according to claim 1, further comprising:
   a second linear member including:
      a distal most end along an extending direction of the second linear member, the distal most end including a knot disposed proximally relative to the second band along a longitudinal direction of the hood; and
      a middle part disposed distally relative to the first band along the longitudinal direction of the hood.

14. The mucous membrane lifting instrument according to claim 11, wherein the second linear member further includes:
   a first part disposed between the first band and the outer peripheral surface of the hood; and
   a second part disposed between the second band and the outer peripheral surface of the hood.

15. The mucous membrane lifting instrument according to claim 12, wherein the second linear member further includes:
   a first part disposed between the first band and the outer peripheral surface of the hood; and
   a second part disposed between the second band and the outer peripheral surface of the hood.

16. The mucous membrane lifting instrument according to claim 1, wherein
   a distal end of the linear member is fixed to the first band.

* * * * *